United States Patent [19]

Kunz et al.

[11] Patent Number: 4,968,344
[45] Date of Patent: Nov. 6, 1990

[54] METHOD FOR PROTECTING PLANTS AGAINST DISEASES

[75] Inventors: Walter Kunz, Oberwil; Theodor Staub, Riehen; Jean-Pierre M/ traux, Basel; Karl Hoegerle, Basel; Robert Nyfeler, Basel; Patricia A. Ahl Goy, Basel, all of Switzerland

[73] Assignee: Ciba-Geigy Corporation, Ardsley, N.Y.

[21] Appl. No.: 429,884

[22] Filed: Oct. 31, 1989

Related U.S. Application Data

[63] Continuation-in-part of Ser. No. 228,777, Aug. 4, 1988, abandoned, which is a continuation of Ser. No. 99,035, Sep. 21, 1987, abandoned.

[30] Foreign Application Priority Data

Sep. 26, 1986 [CH] Switzerland .................. 3866/86
Jul. 17, 1987 [CH] Switzerland .................. 2730/87

[51] Int. Cl.⁵ .................. A01N 9/22; C07D 213/86
[52] U.S. Cl. .................. 71/94; 546/193; 546/314; 546/326; 544/124
[58] Field of Search .................. 546/193, 314, 326; 544/124; 71/94

[56] References Cited

U.S. PATENT DOCUMENTS

| | | | |
|---|---|---|---|
| 4,137,067 | 1/1979 | Gätzi .................. | 71/94 |
| 4,203,988 | 5/1980 | Bolhofer et al. .................. | 424/266 |
| 4,614,833 | 9/1986 | Matas et al. .................. | 546/314 |

FOREIGN PATENT DOCUMENTS

| | | | |
|---|---|---|---|
| 302905 | 1/1955 | Switzerland .................. | 546/193 |
| 1135238 | 8/1962 | Switzerland .................. | 546/193 |
| 0923387 | 4/1963 | Switzerland .................. | 546/314 |
| 1334036 | 10/1973 | United Kingdom .................. | 546/193 |

OTHER PUBLICATIONS

Pommer, Pestic. Sci. 1984, vol. 15, 285-295.
Chem. Abstract, vol. 57, (1962), 4769-4770.
Beilsteins Handbuch Der Organischen Chemie, (1935), p. 48.

*Primary Examiner*—John M. Ford
*Assistant Examiner*—Zinna Nothington-Davis
*Attorney, Agent, or Firm*—Edward McC. Roberts; George R. Dohmann

[57] ABSTRACT

A process for immunizing healthy plants against plant diseases which process comprises the dressing and/or coating of seeds or the treatment of plants and/or their environment by using active ingredients of the formula

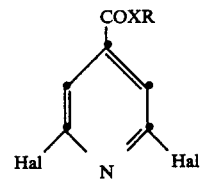

in which
  Hal is halogen,
  X is oxygen or sulfur, and
  R is hydrogen, $C_1$-$C_6$-alkyl, $C_1$-$C_6$-alkyl which interrupted by an oxygen or sulfur atom, $C_1$-$C_6$-alkyl which is substituted by halogen, cyano or the COO—$C_1$-$C_6$-alkyl radical, $C_3$-$C_5$-alkenyl which is unsubstituted or substituted by halogen, $C_3$-$C_5$-alkynyl which is unsubstituted or substituted by halogen, $C_3$-$C_6$-cycloalkyl which is unsubstituted or substituted by halogen or methyl, or a normal equivalent of a cation which is formed from a base or a basic compound.

16 Claims, No Drawings

METHOD FOR PROTECTING PLANTS AGAINST DISEASES

CROSS REFERENCE TO RELATED APPLICATION

This is a continuation-in-part of Ser. No. 228,777, filed on Aug. 4, 1988 now abandoned which is a continuation of Ser. No. 099,035, filed Sept. 21, 1987 abandoned.

The present invention relates to a process for immunizing healthy plants against the infestation of the plants by phytopathogenic microorganisms, in particular by fungi. The process according to the invention comprises the application of special rates of active substances to plants to be immunized against plant diseases and comprises the dressing of seeds by active substances by which procedure plants cultivated from these seeds being immunized against plant diseases. The active substances employed are compounds of the following general formula I:

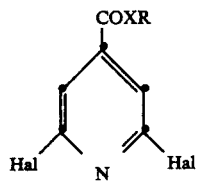
(I)

in which
Hal is halogen,
X is oxygen or sulfur, and
R is hydrogen, $C_1$–$C_6$-alkyl, $C_1$–$C_6$-alkyl which is interrupted by an oxygen or sulfur atom, $C_1$–$C_6$-alkyl which is substituted by halogen, cyano or the COO-$C_1$–$C_6$-alkyl radical, $C_3$–$C_5$-alkenyl which is unsubstituted or substituted by halogen, $C_3$–$C_5$-alkynyl which is unsubstituted or substituted by halogen, $C_3$–$C_6$-cycloalkyl which is unsubstituted or substituted by halogen or methyl, or a normal equivalent of a cation which is formed from a base or a basic compound.

Itself or as a component of another substituent, halogen is fluorine, chlorine, bromine or iodine, preferably chlorine, bromine or iodine.

Itself or as a component of another substituent, alkyl is to be understood as meaning straight-chain or branched alkyl. Depending on the number of carbon atoms specified, it is one of the following groups, for example: methyl, ethyl and the isomers of propyl, butyl, pentyl or hexyl, such as, for example, isopropyl, isobutyl, tert.-butyl, sec.-butyl or isopentyl. Cycloalkyl is any one of cyclopropyl, cycLobutyl, cyclopentyl or cyclohexyl.

Alkenyl is, for example, 1-propenyl, allyl, 1-butenyl, 2-butenyl or 3-butenyl, and also chains having several double bonds. Alkynyl is, for example, 2-propynyl, 1-butynyl, 2-butynyl, 4-pentynyl etc, preferably propargyl.

Possible bases or compounds of a basic character are inorganic or organic bases or base formers. Thus, for example, inorganic bases are to be understood as meaning hydroxides, carbonates and hydrogen carbonates of alkali and alkaline-earth metals, preferably LiOH, NaOH, KOH, Mg(OH)$_2$ or Ca(OH)$_2$; and furthermore NaHCO$_3$, KHCO$_3$, Na$_2$CO$_3$ and K$_2$CO$_3$. Organic bases are to be taken as meaning aliphatic alkylamines having 1 to 3 ($C_1$–$C_6$)-alkyl groups, which can be interrupted by an oxygen atom or several oxygen atoms. Amongst these, alkylamines containing $C_1$–$C_3$-alkyl groups, for example tertiary amines, such as trimethylamine, triethylamine or tripropylamine, and, for example, the amine N(C$_2$H$_4$-OC$_2$H$_5$)$_2$CH$_3$, are preferred. Organic bases are furthermore to be understood as meaning cyclic alkylamines, which are represented by the following compounds: heterocyclic amines of the morpholine type of the formulae A$_1$ and A$_2$

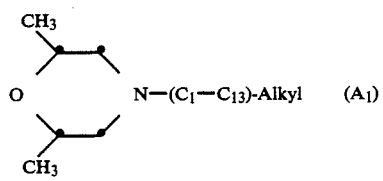 (A$_1$)

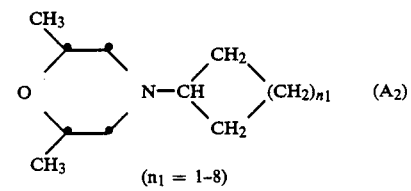 (A$_2$)

($n_1$ = 1–8)

such as, for example,

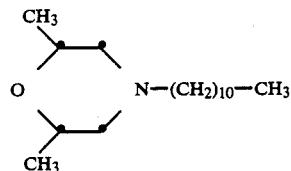

such as, for example,

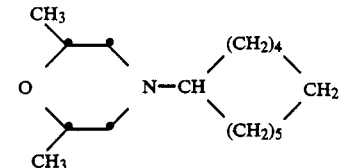

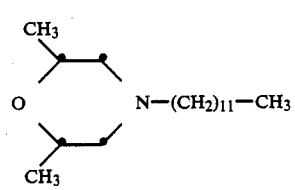

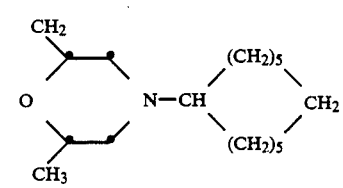

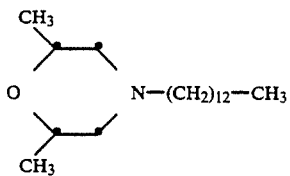

or of the type of the formula B

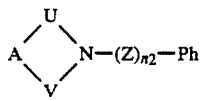 (B)

in which

A is oxygen or the methylene group;

U and V are $C_1$-$C_3$-alkylene or $C_1$-$C_3$-alkylalkylene, preferably ethylene which is unsubstituted or substituted by ethyl;

Z is $C_1$-$C_4$-alkylene, for example the

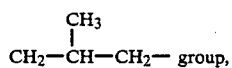 group, and

Ph is phenyl which is unsubstituted or substituted by $C_1$-$C_4$-alkyl, preferably 4-tert.-butyl, and $n_2$ is 0 or 1, in particular including, for example, the compound $B_1$

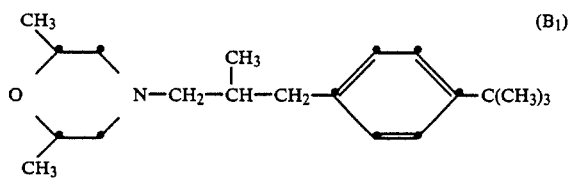 (B₁)

or the compound $B_2$

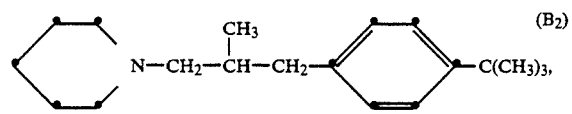 (B₂)

including the enantiomers arising as a consequence of chiral structures of the cationic compounds of the formulae (A) and (B).

Specifically, that configuration of the compound $B_1$ is preferred in which the two methyl groups on morpholine are in the cis-position to one another. Of the two enantiomeric cis-forms, the (−)-configuration is furthermore particularly preferred. The cis-configuration of the formula $B_1$ can be represented by the following formula:

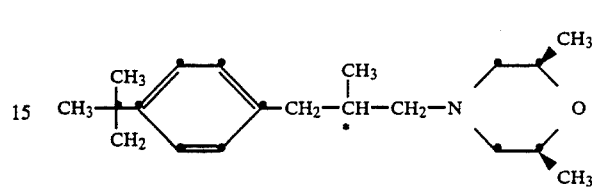

As a consequence of their pronounced immunizing activity against fungal infestation, those active substances are preferred which have the following substituents or combinations of these substituents with one another:

(1) X is oxygen;

(a) according to the following sequence of preference, Hal is: chlorine, bromine, iodine or fluorine, in particular chlorine or bromine, substitution of the 2- and 6-position with identical halogen atoms being preferred, and R is hydrogen, methyl, ethyl, n-propyl, iso-propyl or n-butyl or, as a normal equivalent of a cation: sodium, 4-[3-(4-tert.butylphenyl)-2-methylprop-1-yl]-2,6-dimethylmorpholine or N-[3-(4-tert.butylphenyl)-2-methylprop-1-yl]piperidine or 4-cyclodecyl-2,6-dimethylmorpholine;

(b) Hal is 2,6-dichlor, 2,6-dibromo or 2,6-diiodo, and R is hydrogen, methyl or ethyl, or, as a normal equivalent of a cation 4-[3-(4-tert.butylphenyl)-2-methylprop-1-yl]-2,6 -dimethylmorpholine or N-[3-(4-tert.butylphenyl)-2-methylprop-1-yl]-pyrimidine.

(2) X is sulfur;

(a) according to the following sequence of preference,

Hal is: chlorine, bromine, iodine or fluorine, in particular chlorine or bromine, substitution of 2- and 6-position with identical halogen atoms being preferred, and R is hydrogen, methyl or ethyl, or, as a normal equivalent of a cation: sodium, 4-[3-(4-tert.butylphenyl)-2-methylprop-1-yl]-2,6-dimethylmorpholine or N-[3-(4-tert.butylphenyl)-2-methylprop-1-yl]-piperidine;

(b) Hal is 2,6-dichloro or 2,6-dibromo, and R is hydrogen or methyl, or as a normal equivalent of a cation: 4-[3-(4-tert.butylphenyl)-2-methylprop-1-yl]-2,6-dimethylmorpholine or N-[3-(4-tert.butylphenyl)-2-methylprop-1-yl]-piperidine.

Some of the compounds of the formula I are novel, and some are known. Thus, in Swiss Patent Specification No. 384,929 and British Patent Specification No. 923,387, 2,6-dihaloisonicotinic acid derivatives, for example the free acid and some of its esters and salts, are described as herbicides. Furthermore, in U.S. Pat. No. 4,137,067 and Canadian Patent Specification No. 1,072,443, alkyl 2,6-dichloroisonicotinates are described as intermediates for the preparation of hydrazide derivatives, described as fungicidally active, of previously known isonicotinic acid compounds. In addition, 2,6-dihaloisonicotinic acid derivatives have been disclosed as tuberculostatics (cf. Acta Fac. Pharm. Brun. Bratislav. 4, 65–66 [1962]; Chem. Abstr. Vol. 57, 1962, 4769a). The invention also relates to the novel compounds of the formula I, in particular the salts with organic bases.

The novel compounds of the present invention come as subgroups of the formula I under the following general formulae:

(1) formula I′

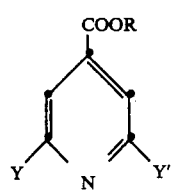

in which

Y and Y′ are halogen, and

R is hydrogen, $C_1$–$C_6$-alkyl, $C_1$–$C_6$-alkyl which is interrupted by an oxygen or sulfur atom, $C_1$–$C_6$-alkyl which is substituted by halogen, cyano or the COO-$C_1$–$C_6$-alkyl radical, $C_3$–$C_5$-alkenyl which is unsubstituted or substituted by halogen, $C_3$–$C_5$-alkynyl which is unsubstituted or substituted by halogen, or $C_3$–$C_6$-cycloalkyl which is unsubstituted or substituted by halogen or methyl, with the proviso that (1) if Y and Y′ are chlorine, R is not hydrogen, $C_1$–$C_3$-alkyl, n-butyl, tert.butyl, allyl, 2-methoxyethyl, 2-ethoxyethyl, β-chlorethyl or methallyl; or (2) if Y and Y′ are bromine, R is not hydrogen, methyl or ethyl; or (3) if Y and Y′ are iodine, R is not hydrogen, ethyl or n-propyl, or (4) if Y and Y′ are fluorine, R is not hydrogen.

(2) formula I″

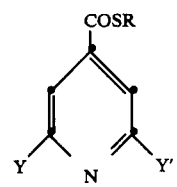

in which

Y and Y′ are halogen, and

R is hydrogen, $C_1$–$C_6$-alkyl, $C_1$–$C_6$-alkyl which is interrupted by an oxygen or sulfur atom, $C_1$–$C_6$-alkyl which is substituted by halogen, cyano or the COOC-$C_1$–$C_6$-alkyl radical, $C_3$–$C_5$-alkenyl which is unsubstituted or substituted by halogen, $C_3$–$C_5$-alkynyl which is unsubstituted or substituted by halogen, or $C_3$–$C_6$-cycloalkyl which is unsubstituted or substituted by halogen or methyl, with the proviso that if Y and Y′ are chlorine, R is not methyl or n-butyl.

(3) Formula $I^{IV}$

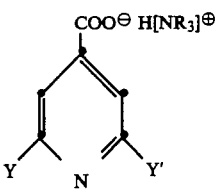

in which

Y and Y′ are halogen, [NR$_3$] is an alkylamine having 1 to 3 ($C_1$–$C_6$)-alkyl groups or an alkylamine having 1 to 3 ($C_1$–$C_6$)-alkyl groups which is interrupted by one or more oxygen atoms, or, furthermore, is one of the following cyclic alkylamines:

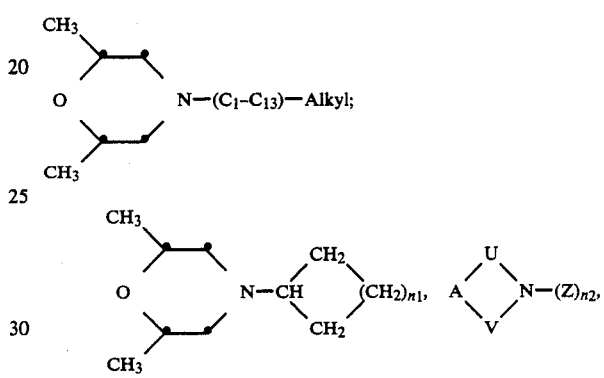

in which n$_1$ is 1–8;

in which A is oxygen or the methylene group, U and V are $C_1$–$C_3$-alkylene or $C_1$–$C_3$-alkylalkylene, Z is $C_1$–$C_4$-alkylene, Ph is phenyl which is unsubstituted or substituted by $C_1$–$C_4$-alkyl, and n$_2$ is 0 or 1, including the enantiomers of the chiral structures of the cyclic alkylamines.

Due to their excellent biological activity, the following compounds are preferred:

Group A (known compounds)

2,6-Dichloroisonicotinic acid (comp. 1.1);
methyl 2,6-dichloroisonicotinate (comp. 1.2);
ethyl 2,6-dichloroisonicotinate (comp. 1.3);
2,6-dibromoisonicotinic acid (comp. 1.10).

Group B (novel compounds)

salt of 2,6-dichloroisonicotinic acid with N-[3-(4-tert.butylphenyl)-2-methyl-n-prop-1-yl]-2,6-dimethylmorpholine (comp. 4.8);

salt of 2,6-dichloroisonicotinic acid with N-[3-(4-tert.butylphenyl)-2-methyl-n-prop-1-yl]-piperidine (comp. 4.9);

propargyl 2,6-dichloroisonicotinate (comp. 1.29);
cyclohexyl 2,6-dichloroisonicotinate (comp. 1.25);
methyl 2,6-difluoroisonicotinate (comp. 1.36).

Surprisingly, it has now been found that the compounds of the formula I prevent infestation of healthy plants by harmful microorganisms through their use according to the invention and thus prevent infestation-caused damage to plants. The major advantage of the process according to the invention for treatment of plants is that, instead of direct action of chemical substances on the plant-damaging micro-organisms, activation and stimulation of the plant's inherent biological defence system occurs before infestation of the plants, so that preservation of the health of the treated plants can be ensured from their own strength without further direct use of microbicides during the vegetation period. It is thus characteristic of the active ingredients of the formula I that they do not exert any direct action on the harmful organisms, but instead have an immunizing action on healthy plants against plant diseases. It was not possible to detect direct action against representatives of the most important groups of fungi (e.g. Fungi Imperfecti, Oomycetes and Actinomycetes). Accordingly, disadvantageous side-effects, as can otherwise be seen to a varying extent in the case of direct combating of parasites on plants by chemical substances, are avoided through the use according to the invention of the compounds of the formula I, which advantageously results in full, uninterrupted growth of the plants.

The mode of action, on which the invention is based, of the compounds of the formula I is at the same time aimed at a general increase in the readiness for defence of the treated plants, so that a general antimicrobial resistance against a wide range of harmful microorganisms is thereby achieved. The process according to the invention is therefore particularly suitable for practical applications. The inherent systemic activity of the compounds of the formula I means that the protective effect also extends to growing plant parts of the treated plants.

The immunizing process according to the invention is effective against the following harmful organisms: fungi, such as, for example, Oomycetes (e.g. *Plasmopare viticola, Peronospora tabacina* and *Phytophtora infestans*), Fungi imperfecti (e.g. *Colletotrichum lagenarium, Piricularia oryzae* and *Cercospora nicotinae*) and Ascomycetes (e.g. *Venturia inaequalis, Erysiphe raminis, Helminthosporium gramineum*); bacteria, such as, for example, Pseudomonades (*Pseudomonas lachrymans, Pseudomonas tomato* and *Pseudomonas tabaci*); Xanthomonades (e.g. *Xanthomonas oryzae* and *Xanthomonas vesicatoria*); and Erwinia (e.g. *Erwinia amylovora*); and viruses, such as, for example, tobacco mosaic virus.

The process according to the invention can be employed for protecting plants of various crops.

In the context of this invention, the following species of plant, for example, apply to the areas of indication disclosed herein: cereals (wheat, barley, rye, oats, rice, sorghum and the like); beet (sugar beet and turnips); pomes, drupes and soft fruit (apples, pears, plums, peaches, almonds, cherries, strawberries, raspberries and blackberries); legumes (beans, lentils, peas and soybeans); oil crops (rape, mustard, poppies, olives, sunflowers, coconuts, castor beans, cocoa and peanuts); cucurbits (pumpkins, cucumbers and melons); fibrous plants (cotton, flax, hemp and jute); citrus fruit, oranges, lemons, grapefruit and mandarins); vegetable types (spinach, lettuce, asparagus, cabbage, carrots, onions, tomatoes, potatoes and peppers); lauraceae (avocado, cinnamon and camphor), or plants such as maize, tobacco, nuts, coffee, sugar cane, tea, grapevines, hops, bananas and natural rubber plants, and also to ornamental plants (flowers, shrubs, deciduous trees and coniferous trees such as conifers). This list does not represent a limitation.

The following plants are to be regarded as particularly suitable target crops for the application of the process according to the invention: cucumber, tobacco, vines, rice, pears, peppers, potatoes, tomatoes and apples.

The compounds of the formula I can be prepared by the following processes via 2,6-dihaloisonicotinic acid or its derivatives as intermediates:

(A) 2,6-Dichloroisonicotinic acid and derivatives

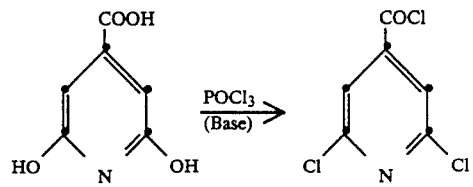

The reaction with POCl₃ takes place in amounts or in excess under a pressure of 1–100×10⁵ Pa, preferably 30–100×10⁵ Pa, and a temperature of 50°–160° C., if appropriate in the presence of a base. Suitable bases are, for example, N,N-dimethylaniline, lutidine or pyridine (Lit. Houben-Weyl, 5/3, p. 925).

The product is subsequently esterified or hydrolyzed using an alcohol appropriate for the ester desired.

The esterification is carried out using an alcohol in excess at temperatures of 0°–80° C., preferably 0°–30° C. Starting from the free acid, the esterification can also be carried out, for example, in the presence of dicyclohexylcarbodiimide or using carbonyldiimidazole.

The esters can also be obtained directly from the reaction mixture by solvolysis using the appropriate alcohol.

(B) 2,6-Dibromoisonicotinic acid and derivatives

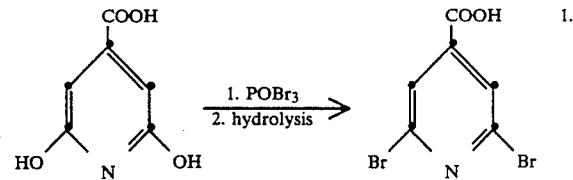

The reaction takes place at temperatures of 50°–200° C. under a pressure of 1–100×10⁵ Pa.

2. By transhalogenation of 2,6-dichloroisonicotinic acid derivatives using alkali metal bromides, for example NaBr or KBr, in dipolar aprotic solvents, if appropriate in the presence of a catalyst, such as, for example, a crown ether (15-crown-5 ether or 18-crown-6 ether).

3. By transhalogenation of 2,6-dichloroisonicotinic acid or derivatives thereof, such as acid halides or homogeneously or mixed acid anhydrides using gaseous hydrobromic acid in an inert organic solvent, preferably a halogenated or nonhalogenated carboxylic acid, such as, for example, acetic acid, propionic acid, trichloroacetic acid, trifluoroacetic acid, tribromoacetic acid, preferably acetic acid, at temperatures of 20°–150° C., preferably 60°–120° C., under a pressure of $1$–$100 \times 10^5$ Pa, preferably under atmospheric pressure.

The product is subsequently esterified using an alcohol appropriate for the ester desired (cf. Acta Fac. Pharm. Bohemoslovenica IV, 1962, 65) or hydrolyzed.

(C) 2,6-Diiodoisonicotinic acid and derivatives

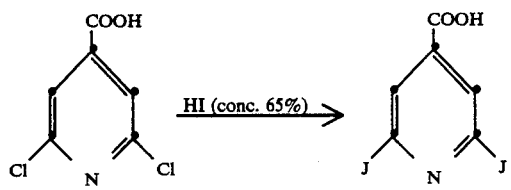

1. The reaction is carried out at a temperature above 50° C.

2. By transhalogenation of 2,6-dichloroisonicotinic acid derivatives using alkali metal iodides in dipolar aprotic solvents, if desired in the presence of a catalyst, for example red phosphorus or a crown ether.

3. The product is subsequently esterified using an alcoholic compound appropriate for the ester desired (cf. Acta Fac. Pharm. Bohemoslovenica IV, 1962, 65) or hydrolyzed.

(D) 2,6-Difluoroisonicotinic acid and derivatives

1. By transhalogenating 2,6-dichloro- or 2,6-dibromoisonicotinic acid derivatives using alkali metal fluorides, preferably CsF, in dipolar aprotic solvents, for example sulfolane, dimethyl sulfoxide or dimethyl sulfone, or in a melt at temperatures of 50°–400° C.

2. By heating 2,6-dichloroisonicotinyl chloride with KF in the presence of $SbF_5$ as catalyst (formed from $Sb_2O_3$ and KF) in a pressure tube at temperatures of 100°–400° C.

3. By diazotizing 2,6-diaminoisonicotinic acid esters in aqueous medium and subsequently reacting the diazonium salt in hydrogen fluoride at temperatures of 0°–100° C., if desired in an autoclave under a pressure of $1$–$100 \times 10^5$ Pa.

The product is subsequently esterified using an alcohol appropriate for the ester desired, the esterification preferably being carried out directly without isolating the acid fluoride, or hydrolyzed.

Suitable solvents for the reactions of the (B2) and (C2) and (D1) types are, for example, dimethylformamide, dimethyl sulfoxide, sulfolane or hexamethylphosphoric triamide.

The preparation processes described under A–D represent part of the present invention. The method specified under (B3) represents a novel, chemically original preparation process.

The inorganic salts of the formula I are prepared by reacting the acids of the formula I with inorganic bases in inert organic solvents at temperatures of 0°–150° C., preferably 10°–50° C.

The organic salts of the formula I are prepared by reacting the acids of the formula I with organic bases, such as aliphatic or cyclic amines, in inert organic solvents at temperatures of 0°–180° C., preferably 10°–50° C., under a pressure of $1$–$100 \times 10^5$ Pa, preferably at atmospheric pressure.

Suitable inert organic solvents for use in salt formation are cyclic ethers, for example dioxane or tetrahydrofuran, alcohols, for example methanol, ethanol, n-propanol or isopropanol, and, furthermore, dipolar aprotic solvents, for example dimethylformamide or dimethyl sulfoxide.

The microbicides which are used in the context of the invention and which contain the compounds of the formula I as active ingredients should be regarded as part of the invention.

Active ingredients of the formula I are usually used in the form of compositions and can be applied simultaneously or successively with further active ingredients to the plants or their environment. These further active ingredients can be fertilizers, micronutrient donors or other preparations which influence plant growth. However, they can also be selective herbicides, insecticides, fungicides, bactericides, nematocides, molluscicides or mixtures of several of these preparations, if appropriate together with further excipients, surfactants or other application-promoting additives which are conventional in formulation technology.

Suitable excipients and additives may be solid or liquid and correspond to the substances which are expedient in formulation technology, for example natural or regenerated mineral substances, solvents, dispersants, wetting agents, adhesives, thickeners, binders or fertilizers.

A preferred method of applying an active ingredient of the formula I, or an agrochemical agent which contains at least one of these active ingredients, is application to the leaves (foliar application). However, the active ingredients of the formula I can also reach the roots of the plants (systemic action) via the soil by soaking the location of the plants with a liquid preparation or incorporating the substances in solid form into the soil, for example in the form of granules (soil application). The compounds of the formula I may also be applied to the seed (coating) either by soaking the seed in a liquid preparation of the active ingredient or by coating it with a solid preparation (dressing).

In these methods of application, the compounds of the formula I are employed in unmodified form or, preferably, together with the auxiliaries which are conventional in formulation technology. For this purpose, they are processed in a known fashion, for example into emulsion concentrates, coatable pastes, directly sprayable or dilutable solutions, diluted emulsions, wettable powders, soluble powders, dusts, granules, or, by encapsulation, into polymeric substances, for example. The methods of application, such as spraying, atomizing, dusting, scattering, coating or watering, are selected according to the intended objectives and the given circumstances, as is the type of agent. The rates for application to plants and/or their environment according to the invention are 100 g to 600 g of active substance (AS) per ha. In the case of seed coating or dressing the application rates are generally 50 g to 250 g of active substance (AS) per 100 kg of seeds and preferable 60 g to 180 g AS per 100 kg of seeds.

The formulations, i.e. the agents, preparations and compositions containing the active ingredient of the formula I and, if desired, a solid or liquid additive, are prepared by intimate mixing and/or grinding of the active ingredients with extenders, for example with solvents or solid excipients, and, if desired, surface-active compounds (surfactants).

Suitable solvents may be: aromatic hydrocarbons, preferably the $C_8$ to $C_{12}$ fractions, for example xylene mixtures or substituted naphthalenes, phthalates, such as dibutyl or dioctyl phthalate, aliphatic hydrocarbons, such as cyclohexane or paraffins, alcohols and glycols and the ethers and esters thereof, such as ethanol, ethylene glycol, ethylene glycol monomethyl or ethyl ether, ketones, such as cyclohexanone, strongly polar solvents, such as N-methyl-2-pyrrolidone, dimethyl sulfoxide or dimethylformamide, and also free or epoxidized vegetable oils, such as epoxidized coconut oil or soya oil; or water.

In general, the solid excipients used, for example for dusts and dispersible powders, are ground natural minerals, such as calcite, talc, kaolin, montmorillonite or attapulgite. In order to improve the physical properties, highly disperse silica or highly disperse sorptive polymers may also be added. Suitable granulated, adsorptive granulate excipients are porous types, for example pumice, broken brick, sepiolite or bentonite, and suitable nonsorptive excipient materials are, for example, calcite or sand. In addition, a large number of pregranulated materials of an inorganic or organic nature, in particular dolomite or pulverized plant residues, can be used. Particularly advantageous application-promoting additives are furthermore natural (animal or vegetable) or synthetic phospholipids from the series comprising the cephalins and lecithins.

Depending on the type of the active ingredient of the formula I to be formulated, possible surface-active compounds are nonionogenic, cationic and/or anionic surfactants having good emulsifying, dispersing and wetting properties. Surfactants are also to be taken as meaning surfactant mixtures.

The cationic surfactants are, in particular, quaternary ammonium salts which contain at least one alkyl radical having 8 to 22 C atoms as N-substituent and unhalogenated or halogenated lower alkyl, benzyl or lower hydroxyalkyl radicals as further substituents.

Suitable anionic surfactants are both so-called water-soluble soaps and water-soluble, synthetic surface-active compounds.

Soaps are the alkali metal, alkaline-earth metal or unsubstituted or substituted ammonium salts of higher fatty acids ($C_{10}$–$C_{22}$), for example the Na or K salts of oleic or stearic acid or of natural fatty acid mixtures, which may be obtained, for example, from coconut oil or tallow oil.

The synthetic surfactants used can be, in particular, fatty alcohol sulfonates, fatty alcohol sulfates, sulfonated benzimidazole derivatives or alkylsulfonates. The fatty alcohol sulfonates or sulfates are generally present as alkali metal, alkaline-earth metal or unsubstituted or substituted ammonium salts and contain an alkyl radical having 8 to 22 C atoms.

Suitable nonionic surfactants are primarily polyglycol ether derivatives of aliphatic or cycloaliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkyl phenols.

The agents may also contain further additives, such as stabilizers, defoamers, viscosity regulators, binders, adhesives and fertilizers or other active ingredients for achieving specific effects.

The agrochemical preparations generally contain 0.1 to 99% by weight, in particular 0.1 to 95% by weight, of the active ingredients of the formula I, 99.9 to 1% by weight, in particular 99.8 to 5% by weight, of a solid or liquid additive and 0 to 25% by weight, in particular 0.1 to 25% by weight, of a surfactant.

The following examples serve to illustrate the invention in greater detail, without representing a limitation.

RT=room temperature; DMF=dimethylformamide; THF=tetrahydrofuran.

1. Preparation examples

EXAMPLE 1.1

Preparation of ethyl 2,6-dichloroisonicotinate

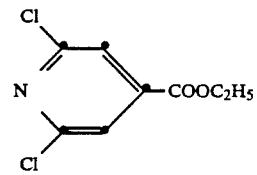

189.4 g of 2,6-dichloroisonicotinyl chloride are added dropwise with stirring to 3.6 liters of absolute ethanol at RT with exclusion of moisture. During this addition, the internal temperature rises to 33° C. The reaction is continued to completion overnight with stirring. The crystalline material (needles) remaining after evaporation is taken up in ether, washed with 5% sodium hydrogen carbonate solution and water, dried and evaporated. 191.2 g of white needles of melting point 64°–6° C. are obtained.

The 2,6-dichloroisonicotinyl chloride required as starting material is prepared as described, for example, in Helv. Chim. Acta 30, 507 (1947).

EXAMPLE 1.2

Preparation of 2,6-diiodoisonicotinic acid

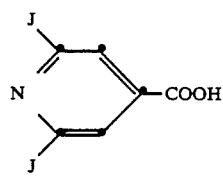

The compound is prepared in accordance with Acta virol. 17, 326 (1971). Its melting point is 193°–195° C.

EXAMPLE 1.3

Preparation of thioethyl 2,6-dichloroisonicotinate

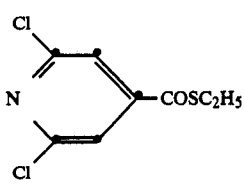

0.7 g of 4-dimethylaminopyridine and 5.0 ml of ethyl mercaptan are added to a solution of 11.5 g of 2,6-dichloroisonicotinic acid in 90 ml of absolute DMF. To this mixture, a solution of 12.3 g of dicyclohexylcarbodiimide in 30 ml of absolute DMF is added dropwise with cooling at 5°-10° C. The mixture is stirred overnight at RT, the precipitated dicyclohexylurea is filtered off on the next day and washed with DMF, and the filtrate is distributed between water and methylene chloride. The organic phase is washed three times with water, dried over sodium sulfate, filtered and evaporated. After distillation in a bulb tube at 150°-160° C./11.7 Pa, 10.2 g of white crystals of melting point 38°-39° C. are produced.

EXAMPLE 1.4

Conversion of 2,6-dichloroisonicotinic acid into the sodium salt

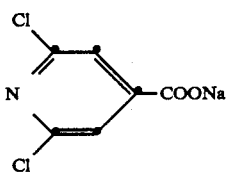

5 g of 2,6-dichloroisonicotinic acid are dissolved in 10 ml of absolute THF and treated with 27.7 ml of 1N sodium hydroxide solution with cooling. After stirring briefly at RT, the mixture is evaporated, and traces of water still present are removed by repeated addition of toluene and azeotropic distillation. The salt remaining is dried at 50° C. in a high vacuum. 5.3 g of a white powder, melting point >220° C., are produced.

EXAMPLE 1.5

Conversion of 2,6-dichloroisonicotinic acid into the triethylammonium salt

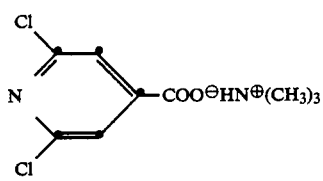

5 g of 2,6-dichloroisonicotinic acid are dissolved in 10 ml of absolute THF. 3.6 ml of absolute triethylamine are subsequently added dropwise after cooling, and the solution is stirred at RT for 10 minutes. The mixture is subsequently evaporated on a rotary evaporator, and the amorphous residue remaining is dried in a high vacuum. The yield of the final product of melting point 101°-104° C. is 6.4 g.

EXAMPLE 1.6

Preparation of methyl 2,6-difluoroisonicotinate 244 g of potassium fluoride and 1.5 g of antimony trioxide are mixed thoroughly and introduced alternately with 73.5 g of 2,6-dichloroisonicotinyl chloride in the thinnest possible layers into a pressure tube. The contents are warmed at 260° C. for 20 hours, a pressure of $1.3 \times 10^6$ Pa building up.

After cooling, the contents are introduced into 250 ml of methanol with vigorous stirring and continuing cooling at a maximum of 30° C., and the mixture is stirred at RT overnight. The mixture is then filtered and evaporated, and the residue is distilled. Boiling point 81°-82° C./$1.3 \times 10^3$ Pa.

EXAMPLE 1.7

Preparation of 2,6-difluoroisonicotinic acid 22.6 g of methyl 2,6-difluoroisonicotinate are dissolved in 25 ml of dioxane and added to a mixture of 150 ml of conc. hydrochloric acid and 100 ml of water. The mixture is then refluxed for 2¼ hours, volume is reduced to about ⅔ by evaporation, and the residue is cooled. The acid which precipitates out in crystalline form is filtered off and dried.

Melting point 152°-154° C.

EXAMPLE 1.8

Preparation of 2,6-dibromoisonicotinic acid

Gaseous hydrobromic acid is passed into a boiling solution of 114 g of 2,6-dichloroisonicotinic acid in 1.6 liters of acetic acid* with stirring until the reaction is complete (280 g of HBr in the course of 2 days). The course of the reaction is checked by means of NMR measurements. When the reaction is complete, the mixture is evaporated in vacuo, and the residue is treated with ice water. The precipitate is filtered off, washed with water and taken up in dichloromethane/tetrahydrofuran (4:1). The solution formed is then washed twice with water, dried over potassium sulfate and evaporated. 114.7 g (=83% of theory) of pale brown crystals of melting point 179°-187° C. remain.

\* In place of pure acetic acid, the latter can previously be brought to the desired concentration using HBr, or a commercially available 33% solution of HBr in glacial acetic acid can be employed.

The following compounds can be prepared as described in Examples 1.1-1.8 above.

Compounds of the formula I′

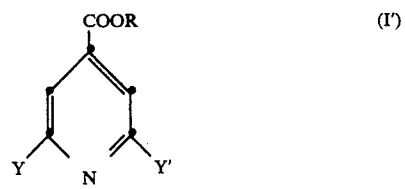

TABLE 1

| Comp. No. | Y | Y′ | R | Physical data |
|---|---|---|---|---|
| (known compounds) | | | | |

TABLE 1-continued

| Comp. No. | Y | Y' | R | Physical data |
|---|---|---|---|---|
| 1.1 | Cl | Cl | H | m.p. 210° C. |
| 1.2 | Cl | Cl | CH$_3$ | m.p. 82° C. |
| 1.3 | Cl | Cl | C$_2$H$_5$ | m.p. 65–66° C. |
| 1.4 | Cl | Cl | C$_3$H$_7$-n | $n_D^{20}$ 1.5257 |
| 1.5 | Cl | Cl | —CH(CH$_3$)$_2$ | m.p. 55–56° C. |
| 1.6 | Cl | Cl | n-C$_4$H$_9$ | $n_D^{28}$ 1.5185 |
| 1.7 | Cl | Cl | —CH$_2$CH=CH$_2$ | $n_D^{28}$ 1.5200 |
| 1.8 | Cl | Cl | —CH$_2$CH$_2$OCH$_3$ | m.p. 60–61° C. |
| 1.9 | Cl | Cl | —CH$_2$CH$_2$OC$_2$H$_5$ | b.p. 114° C./13 Pa |
| 1.10 | Br | Br | H | m.p. 195–196° C. |
| 1.11 | Br | Br | CH$_3$ | m.p. 82–84° C. |
| 1.12 | Br | Br | C$_2$H$_5$ | m.p. 70–72° C. |
| 1.13 | I | I | H | m.p. 193–195° C. |
| 1.14 | I | I | C$_2$H$_5$ | m.p. 117–118° C. |
| 1.15 | F | F | H | m.p. 152–154° C. |
| 1.17 | Cl | Cl | s-C$_4$H$_9$ | |
| 1.18 | Br | Br | t-C$_4$H$_9$ | m.p. 34–37° C. |
| 1.19 | Br | Br | n-C$_5$H$_{11}$ | $n_D^{20}$ 1.5508 |
| 1.20 | Br | Br | i-C$_5$H$_{11}$ | m.p. 62–64° C. |
| 1.21 | Cl | Cl | n-C$_6$H$_{13}$ | |
| 1.22 | Cl | Cl | cyclobutyl | |
| 1.23 | Cl | Cl | cyclopropyl | |
| 1.24 | Cl | Cl | cyclobutyl-methyl | m.p. 38–40° C. |
| 1.25 | Cl | Cl | cyclohexyl | m.p. 87–89° C. |
| 1.26 | Cl | Cl | —CH$_2$CH$_2$CH=CH$_2$ | |
| 1.27 | Cl | Cl | —CH(CH$_3$)CH=CH$_2$ | Oil |
| 1.28 | Br | Br | —CH$_2$—CH$_2$OC$_2$H$_5$ | |
| 1.29 | Cl | Cl | —CH$_2$C≡CH | m.p. 61–63° C. |
| 1.30 | Cl | Cl | —CH$_2$C≡CI | resin |
| 1.31 | Cl | Cl | —CH$_2$CH$_2$C≡CH | |
| 1.32 | Br | Br | C$_3$H$_7$-n | m.p. 82–84° C. |
| 1.33 | Br | Br | i-C$_3$H$_7$ | |
| 1.34 | Br | Br | n-C$_4$H$_9$ | |
| 1.35 | I | I | CH$_3$ | m.p. 122–124° C. |
| 1.36 | F | F | CH$_3$ | b.p. 81–82° C./ 1,3 · 10$^3$ Pa |
| 1.37 | F | F | C$_2$H$_5$ | Oil |
| 1.38 | F | F | i-C$_3$H$_7$ | Oil |
| 1.39 | Cl | Cl | —CH$_2$CCl$_3$ | Oil |
| 1.40 | Br | Br | n-C$_6$H$_{13}$ | |
| 1.41 | I | I | n-C$_5$H$_{11}$ | Oil |
| 1.42 | Br | Br | cyclobutyl-methyl | |
| 1.43 | Br | Br | cyclohexyl | m.p. 102–104° C. |
| 1.44 | I | I | C$_3$H$_7$-n | Oil |
| 1.45 | Br | Br | —CH$_2$-cyclopropyl | $n_D^{20}$ 1.5752 |
| 1.46 | Cl | Cl | —CH$_2$-cyclopropyl | $n_D^{20}$ 1.5415 |
| 1.47 | I | I | cyclobutyl-methyl | m.p. 74–77° C. |
| 1.48 | I | I | —CH$_2$CH$_2$OCH$_3$ | |
| 1.49 | Cl | Cl | —CH(C$_2$H$_5$)$_2$ | Oil |

Compounds of the formula I''

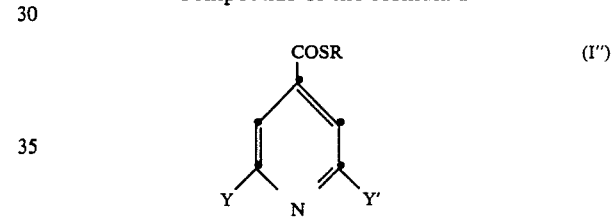

(I'')

TABLE 2

| Comp. No. | Y | Y' | R | Physical data |
|---|---|---|---|---|
| (known compounds) | | | | |
| 2.1 | Cl | Cl | CH$_3$ | Oil |
| 2.2 | Cl | Cl | C$_4$H$_9$-n | Oil |
| (novel Compounds) | | | | |
| 2.3 | Cl | Cl | C$_2$H$_5$ | m.p. 38–39° C. |
| 2.4 | Cl | Cl | C$_3$H$_7$ | $n_D^{20}$ 1.5793 |
| 2.5 | Cl | Cl | CH$_2$CH=CH$_2$ | |
| 2.6 | Br | Br | CH$_3$ | |
| 2.7 | Br | Br | C$_2$H$_5$ | |
| 2.8 | Br | Br | C$_3$H$_7$-n | |
| 2.9 | I | I | CH$_3$ | |
| 2.10 | I | I | C$_2$H$_5$ | |
| 2.11 | I | I | i-C$_3$H$_7$ | |
| 2.12 | F | F | CH$_3$ | Oil |
| 2.13 | F | F | C$_2$H$_5$ | Oil |
| 2.14 | F | F | C$_3$H$_7$-n | Oil |
| 2.15 | Cl | Cl | CH$_2$C≡CH | |

Compounds of the formula I'''

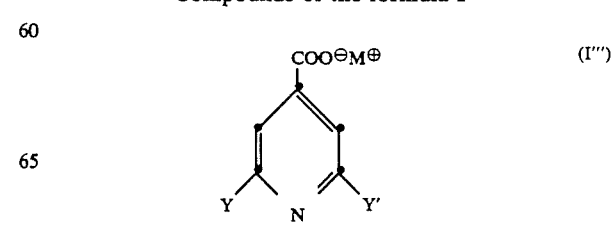

(I''')

TABLE 3

| Comp. No. | Y | Y' | M⊕ | Physical data |
|---|---|---|---|---|
| | | | (known compounds) | |
| 3.1 | Cl | Cl | Na⊕ | m.p. >220° C. |
| 3.2 | Cl | Cl | ½ Ca²⊕ | m.p. >300° C. |
| 3.3 | Br | Br | Na⊕ | m.p. >250° C. |
| 3.4 | I | I | Na⊕ | m.p. >200° C. |
| | | | (novel compounds) | |
| 3.5 | Cl | Cl | ½ Mg²⊕ | m.p. >250° C. |
| 3.6 | Cl | Cl | Li⊕ | m.p. >250° C. |
| 3.7 | Cl | Cl | K⊕ | m.p. >255-265° C. (dec.) |
| 3.8 | Br | Br | Li⊕ | m.p. >200° C. |
| 3.9 | Br | Br | K⊕ | m.p. >250° C. |
| 3.10 | Br | Br | ½ Mg²⊕ | m.p. >250° C. |
| 3.11 | I | I | Li⊕ | |
| 3.12 | I | I | K⊕ | m.p. >220° C. |
| 3.13 | F | F | Na⊕ | |
| 3.14 | F | F | K⊕ | m.p. ≧210° C. |
| 3.15 | F | F | ½ Mg²⊕ | |

Compounds of the formula $I^{IV}$

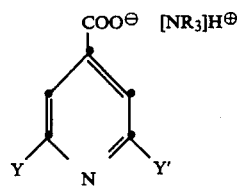

TABLE 4

(novel compounds)

| Comp. No. | Y | Y' | [NR₃] | Physical data |
|---|---|---|---|---|
| 4.1 | Cl | Cl | N(CH₃)₃ | |
| 4.2 | Cl | Cl | N(C₂H₅)₃ | m.p. 101-104° C. |
| 4.3 | Cl | Cl | N(CH₃)(C₂H₅) | |
| 4.4 | Cl | Cl | N(C₂H₅)(i-C₃H₇)₂ | |
| 4.5 | Cl | Cl | CH₃—N(morpholine) | |
| 4.6 | Cl | Cl | CH₃—N(piperidine) | |

| Comp. No. | Y | Y' | [NR₃]H | Physical data |
|---|---|---|---|---|
| 4.7 | Cl | Cl | C₆H₁₃—N(2,6-dimethylmorpholine) | resin |
| 4.8 | Cl | Cl | Fm* | m.p. 155-193° C.** |
| 4.9 | Cl | Cl | Fd* | m.p. 103-104° C. |
| 4.10 | Cl | Cl | Tri* | |
| 4.11 | Cl | Cl | Do* | |
| 4.12 | Br | Br | N(C₅H₅)₃ | |
| 4.13 | Br | Br | N(C₂H₅)(i-C₃H₇)₂ | |
| 4.14 | Br | Br | Tri* | |
| 4.15 | Br | Br | Fd* | |
| 4.16 | Br | Br | Fm* | |
| 4.17 | I | I | N(C₂H₅)₃ | |
| 4.18 | I | I | Fm* | |
| 4.19 | I | I | Fd* | |
| 4.20 | F | F | N(C₂H₅)₃ | |
| 4.21 | F | F | Fd* | |
| 4.22 | F | F | Fm* | |
| 4.23 | Cl | Cl | CH₃N(CH₂CH₂OC₂H₅) | |
| 4.24 | Cl | Cl | C₆H₅CH₂—N(CH₃)₂ | |
| 4.25 | Cl | Cl | C₆H₅N(CH₃)₂ | |
| 4.26 | Cl | Cl | Cydo* | |

**cis-trans mixture

*Fm =
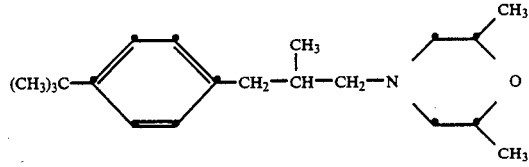

*Fd =
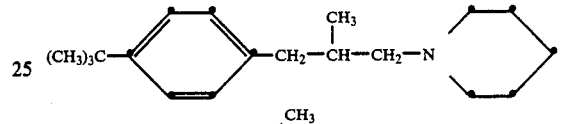

*Do = $C_{12}H_{25}$—N

*Tri = $C_{13}H_{27}$—N

*Cydo =
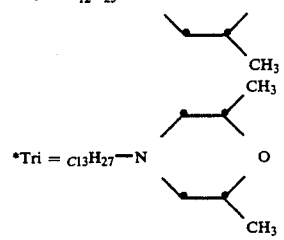

2. Formulation examples for liquid active ingredients of the formula I (%=percent by weight)

| 2.1 Emulsion concentrates | (a) | (b) | (c) |
|---|---|---|---|
| Active ingredient from Tables 1a to 4 | 25% | 40% | 50% |
| Ca dodecylbenzenesulfonate | 5% | 8% | 6% |
| Castor oil polyethylene glycol ether (36 moles of ethylene oxide) | 5% | — | — |
| Tributylphenoyl polyethylene glycol ether (30 moles of ethylene oxide) | — | 12% | 4% |
| Cyclohexanone | — | 15% | 20% |
| Xylene mixture | 65% | 25% | 20% |

Emulsions of any desired concentration can be prepared from such concentrations by diluting with water.

| 2.2 Solution | (a) | (b) | (c) | (d) |
|---|---|---|---|---|
| Active ingredient from Tables 1a to 4 | 80% | 10% | 5% | 95% |

| 2.2 Solution | (a) | (b) | (c) | (d) |
|---|---|---|---|---|
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Petroleum ether (boiling range 160–190° C. | — | — | 94% | — |

(MW = molecular weight)

The solutions are suitable for use in the form of very small drops.

| 2.3 Granules | (a) | (b) |
|---|---|---|
| Active ingredient from Tables 1a to 4 | 5% | 10% |
| Kaolin | 94% | — |
| Highly disperse silica | 1% | — |
| Attapulgite | — | 90% |

The active ingredient is dissolved in methylene chloride and sprayed onto the excipient, and the solvent is subsequently evaporated off in vacuo.

| 2.4 Dusts | (a) | (b) |
|---|---|---|
| Active ingredient from Tables 1a to 4 | 2% | 5% |
| Highly disperse silica | 1% | 5% |
| Talc | 97% | — |
| Kaolin | — | 90% |

Ready-to-use dusts are obtained by mixing the excipients intimately with the active ingredient.

| Formulation examples for solid active ingredients of the formula I (% = percent by weight) | | | |
|---|---|---|---|
| 2.5 Wettable powders | (a) | (b) | (c) |
| Active ingredient from Tables 1a to 4 | 25% | 50% | 75% |
| Na ligninsulfonate | 5% | 5% | — |
| Na Laurylsulfate | 3% | — | 5% |
| Na diisobutylnaphthalenesulfonate | — | 6% | 10% |
| Octylphenol polyethylene glycol ether (7–8 moles of ethylene oxide) | — | 2% | — |
| Highly disperse silica | 5% | 10% | 10% |
| Kaolin | 62% | 27% | — |

The active ingredient is mixed with the additives and ground thoroughly in a suitable mill. Wettable powders are obtained which can be diluted with water to form suspensions of any desired concentration.

| 2.6 Emulsion concentrate | |
|---|---|
| Active Ingredient from Tables 1a to 4 | 10% |
| Octylphenol polyethylene glycol ether (4–5 moles of ethylene oxide) | 3% |
| Ca dodecylbenzenesulfonate | 3% |
| Castor oil polyglycol ether (35 moles of ethylene oxide) | 4% |
| Cyclohexanone | 30% |
| Xylene mixture | 50% |

Emulsions of any desired concentration can be prepared from this concentrate by dilution with water.

| 2.7 Dusts | (a) | (b) |
|---|---|---|
| Active ingredient from Tables 1a to 4 | 5% | 8% |
| Talc | 95% | — |
| Kaolin | — | 92% |

Ready-to-use dusts are obtained by mixing the active ingredient with the excipients and grinding in a suitable mill.

| 2.8 Extruder granules | |
|---|---|
| Active ingredient from Tables 1a to 4 | 10% |
| Na ligninsulfonate | 2% |
| Carboxymethylcellulose | 1% |
| Kaolin | 87% |

The active ingredient is mixed with the additives, ground and moistened with water. This mixture is extruded and subsequently dried in a stream of air.

| 2.9 Coated granules | |
|---|---|
| Active ingredient from Tables 1a to 4 | 3% |
| Polyethylene glycol (MW 200) | 3% |
| Kaolin | 94% |

(MW = molecular weight)

In a mixer, the finely ground active ingredient is applied uniformly to the kaolin, moistened with polyethylene glycol. In this fashion, dust-free coated granules are obtained.

| 2.10 Suspension concentrate | |
|---|---|
| Active ingredient from Tables 1a to 4 | 40% |
| Ethylene glycol | 10% |
| Nonylphenol polyethylene glycol ether (15 moles of ethylene oxide) | 6% |
| N-Ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. A suspension concentrate is thus obtained from which suspensions of any desired concentration can be prepared by dilution with water.

3. Biological examples

EXAMPLE 3.1

Immunizing action against *Colletotrichum lagenarium* on *Cucumis sativus* L.

(a) After raising for 2 weeks, cucumber plants are sprayed with a spray liquor prepared from a wettable powder of the active ingredient (concentration: 20 ppm).

After 3 weeks, the plants are infected with a spore suspension ($1.5 \times 10^5$ spores/ml) of the fungus and incubated for 36 hours at elevated atmospheric humidity and a temperature of 23° C. Incubation is then continued at normal atmospheric humidity and at 22° to 23° C.

The protective action is assessed based on the fungal infestation 7-8 days after infection.

Untreated, but infected control plants have a fungal infestation of 100% in the test.

Compounds from Tables 1a to 4 caused good immunization against *Colletotrichum lagenarium*. Thus, plants which had been treated, for example, with compounds nos. 1.1, 1.2, 1.3, 1.10 or 4.9 remained virtually completely free of Colletotrichum (infestation 10 to 0%).

(b) Cucumber seeds are dressed with a solution of the active ingredient (concentration: 180 g/100 kg of seed). The seeds are sown. After 4 weeks, the plants are infected with a spore suspension ($1.5 \times 10^5$ spores/ml) of the fungus and incubated for 36 hours at elevated atmospheric humidity and a temperature of 23° C. Incubation is then continued at normal atmospheric humidity and at 22° C. to 23° C. The protective action is assessed based on the fungal infestation 7-8 days after infection.

Infected control plants whose seeds were not treated have a fungal infestation of 100% in this test.

Compounds from Tables 1a to 4 caused good immunization against *Colletotrichum laganarium*. Thus, plants whose seeds had been treated, for example, with compound nos. 1.1, 1.2, 1.3, 1.10 or 4.9 remained virtually free of Colletotrichum (infestation 10 to 0%).

EXAMPLE 3.2

Comparison test (direct action against *Colletotrichum lagenarium*)

The formulated active ingredient is mixed with nutrient medium (potato-carrot/agar) in various concentrations (10, 1, 0.1 and 0.01 ppm). The individual nutrient media containing the active ingredient are then poured into Petri dishes. After cooling the mixtures, a mycelium rondelle (8 mm) of *Colletotrichum lagenarium* is placed in the centre of each Petri dish. Incubation subsequently takes place at 22° C. After incubating for 10 days, the diameters of the areas colonized by fungus are measured.

No inhibition of fungal growth was observed in the case of compounds 1.1, 1.2, 1.3, 1.4, 1.5, 1.7, 1.10, 1.11, 1.12, 1.13, 1.16, 1.29, 1.46, 2.3, 3.1, 4.2 and 4.8. In contrast, a 50% inhibition (EC$_{50}$) of *Colletotrichum lagenarium* occurred when the fungicide benomyl (commercial product) was

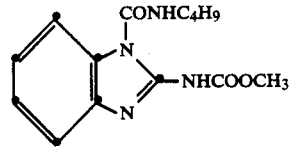

used as comparison substance at 0.1 ppm.

EXAMPLE 3.3

Immunizing against *Pseudomonas lachrymans* on *Cucumis sativus* L.

After raising for 2 weeks, cucumber plants are sprayed with a spray liquor prepared from a wettable powder of the active ingredient (concentration: 20 ppm).

After 1 week, the plants are infected with a bacteria suspension ($10^8$ bacteria/ml) and incubated for 7 days at elevated atmospheric humidity and a temperature of 23° C.

The protective action is assessed based on the bacteria infestation 7-8 days after infection.

Untreated, but infected control plants have an infestation of 100% in the test.

Compounds from Tables 1a to 4 caused good immunization against *Pseudomonas lachrymans*. Thus, plants which had been treated, for example, with compound nos. 1.1, 1.2, 1.3, 1.10 or 4.9 remained virtually completely free of Pseudomonas (infestation 10 to 0%).

EXAMPLE 3.4

Comparison test (direct action against *Pseudomonas lachrymans*

The formulated active ingredient is mixed with autoclaved and cooled nutrient broth (0.8%) at various concentrations (100, 10, 1, 0.1 and 0.01 ppm) and poured into dishes. A bacteria suspension ($10^6$ bacteria/ml) of *Pseudomonas lachrymans* is subsequently pipetted into the dishes. Incubation then takes place at 22° C. in the dark on a vibrator table (120 rpm). After incubating for 10 days, the bacterial growth is determined spectrophotometrically.

No inhibition of bacterial growth was observed in the case, for example, of compounds 1.1 and 1.2. In contrast, a 50% inhibition (EC$_{50}$) of *Pseudomonas lachrymans* took place when the bactericide Streptomycin was used as comparison substance at 1 ppm.

EXAMPLE 3.5

Action against *phytophora parasitica* var. *nicotianae* on tobacco

Systemic action

Tobacco plants (8 weeks old) are treated through soil application (concentration 2 ppm) or injected (200 ppm) with a formulated solution of the active ingredient. After 4 days, the plants are infected with *Phytophthora parasitica*: 2 ml of a zoospore suspension ($8 \times 10^4$ spores/ml) are pipetted around the base of the stem and washed into the soil with water. The plants are kept at 24°-26° C. for 3 weeks.

The symptoms are assessed on the basis of the degree of withering of the plants.

Compounds from Tables 1a to 4 have a good action against *Phytophthora parasitica*. Thus, for example, the compound 1.2 reduces withering to 0-25%.

Untreated, but infected plants were 100% withered.

EXAMPLE 3.6

Action against *Peronospora tabacina* on tobacco (a) Residual protective action

Tobacco plants (8 weeks old) are sprayed with a formulated solution of the active ingredient (concentration: 200 ppm). 4 days after treatment, the plants are inoculated with a sporangium suspension of *Peronospora tabacina* ($10^4$ spores/ml), kept at 25° C. for 20 hours in the dark and elevated atmospheric humidity and then incubated further with the normal day/night alternation.

(b) Systemic action

Tobacco plants (8 weeks old) are treated through soil application with a formulated solution of the active ingredient (concentration: 6 ppm). After 4 days, the plants are inoculated with a sporangium suspension of *Peronospora tabacina* ($10^4$ spores/ml), kept at 25° C. for 20 hours in the dark and elevated atmospheric humidity and then incubated further in the normal day/night alternation.

The symptoms are assessed in tests (a) and (b) based on the leaf surface infested with fungus.

Compounds from Tables 1a to 4 had a good action against *Peronospora tabacina*.

Untreated, but infected plants had an infestation of 90 to 100%.

EXAMPLE 3.7

Action against *Cercospora nicotinae* on tobacco (a) Residual protective action

Tobacco plants (8 weeks old) are injected with a formulated solution of the active ingredient (concentration: 200 ppm). 4 days after treatment, the plants are inoculated with a spore suspension of *Cercospora nicotinae* ($10^5$ spores/ml) and incubated for 5 days at elevated atmospheric humidity and a temperature of 22°–25° C. Incubation is then continued at normal atmospheric humidity and at 20°–22° C.

(b) Systemic action

Tobacco plants (8 weeks old) are treated through soil application with a formulated solution of the active ingredient (concentration: 20 ppm, 6 ppm and 2 ppm). After 4 days, the plants are inoculated with a spore suspension of *Cercospora nicotinae* ($10^5$ spores/ml) and incubated for 5 days at elevated atmospheric humidity and a temperature of 22°–25° C. Incubation is then continued at normal atmospheric humidity and at 20°–22° C.

The symptoms are assessed in tests (a) and (b) based on the fungal infestation 12 to 14 days after infection.

Compounds from Tables 1a to 4 had a good action against *Peronospora nicotinae*. Thus, for example, compounds 1.1, 1.2 and 1.10 reduced fungal infestation to 0–5% in test (a) and compounds 1.2 and 1.3 reduced fungal infestation to 0–20% in test (b).

The control plants had an infestation of 100%.

EXAMPLE 3.8

Action against *Pyricularia oryzae* on rice plants (a) Residual protective action After raising for 2 weeks, rice plants are sprayed with a spray liquor (0.002% of active substance) prepared from a wettable powder of the active ingredient. After 72 hours, the treated plants are infected with a conidia suspension of the fungus. After incubating for 5 days at 95–100% relative atmospheric humidity at 24° C., the fungal infestation is assessed.

(b) Systemic action

A spray liquor (0.006% of active substance, based on the soil volume) prepared from a wettable powder of the active ingredient is poured onto rice plants, 2 weeks old, planted in pots. The pots are then filled with water until the lowermost parts of the stem of the rice plants are standing in water. After 96 hours, the treated rice plants are infected with a conidia suspension of the fungus. After incubating the infected plants for 5 days at 95–100% relative atmospheric humidity and about 24° C., the fungal infestation is assessed.

Rice plants which have been treated with a spray liquor containing as active substance a compound from Tables 1a to 4 had only slight fungal infestation compared to untreated control plants (100% infestation). Thus, for example, compound 1.29 reduced fungal infestation to 5 to 20% in tests (a) and (b).

Comparison test (direct action against *Pyricularia oryxae*

The formulated active ingredient is mixed with autoclaved and cooled nutrient medium (V-8 vegetable juice) at various concentrations (10, 1 and 0.1 ppm) and poured into dishes. A spore suspension (1000 spores/ml) is subsequently pipetted into the dishes. Incubation then takes place at 22° C. in the dark. After 2–3 days, the fungal growth is determined spectrophotometrically.

In the case of compound 1.1, for example, no inhibition of growth of *Pyricularia oryzae* was observed.

In contrast, 50% inhibition ($EC_{50}$) of *Pyricularia oryzae* occurred when the fungicide benomyl (commercial product; see Example 3.2) was used as comparison substance at 0.1 ppm.

EXAMPLE 3.9

Action against *Pseudomonas tabaci* on tobacco (a) Residual protective action

Tobacco plants (8 weeks old) are injected with a formulated solution of the active ingredient (concentration: 200 ppm). After 4 days, the plants are sprayed with a bacteria suspension ($2 \times 10^7$ bacteria/ml) and kept at elevated atmospheric humidity and 22°–25° C. for 3 days. Incubation is then continued at normal atmospheric humidity and 22°–25° C. for 3 days.

(b) Systemic action

Tobacco plants (8 weeks old) are treated through soil application with a formulated solution of the active ingredient (concentration: 20, 6 and 2 ppm). After 4 days, the plants are sprayed with a bacteria suspension ($2 \times 10^7$ bacteria/ml) and kept at elevated atmospheric humidity and 22°–25° C. for 3 days. Incubation is then continued at normal atmospheric humidity and 22°–25° C. for 3 days.

The symptoms are assessed in tests (a) and (b) based on the bacterial infestation.

Untreated, but infected plants had an infestation of 100%. Plants which had been treated in test (a) with compounds 1.2 and 1.3 had an infestation of 0–20%. Plants which had been treated in test (b) with compound 1.2 had an infestation of 0–20%.

(c) Direct action

The active ingredient is mixed with liquid nutrient medium (nutrient broth) containing $10^6$ bacteria/ml at various concentrations (100, 10, 1 and 0.1 ppm) and poured into microtiter plates. The plates are incubated at 22° C., and the growth of the bacteria is determined after 16 hours by measuring the optical density.

When compounds 1.1 and 1.2 were used, for example, no inhibition of growth of the *Pseudomonas tabaci* was observed. In contrast, streptomycin as comparison substance at 0.1 ppm caused a 50 percent inhibition of growth.

EXAMPLE 3.10

Action against tobacco mosaic virus on tobacco (a) Immunizing action

Tobacco plants (8 weeks old) are injected with a formulated solution of the active ingredient (concentration: 200 ppm). After 4 days, the plants are inoculated mechanically with a suspension of tobacco mosaic virus (0.5 μm/ml carborundum) and incubated at a temperature of 20°–22° C.

(b) Direct action

The formulated active ingredient was added directly to the tobacco mosaic virus inoculum (200 ppm+0.5 μg/ml of virus+carborundum). After one hour, tobacco plants (8 weeks old) were inoculated mechanically with the mixture.

The protective action is assessed in tests (a) and (b) based on the number and size of local lesions 7 days after inoculation.

Plants which have been treated with compounds 1.1 and 1.2 had few lesions (15 to 20%) in test (a) compared to untreated, but infected plants, which had an infestation of 100%.

Plants which have been inoculated in test (Lb) with a mixture of viruses and active ingredient had no protective action (100% infestation).

What is claimed is:

1. A method for immunizing healthy plants against the infestation of the plants by the fungi Oomycetes, *Fungi imperfecti* and Ascomycetes and the bacteria Pseudomonades, Xanthomonades and Erwinia and the Tobacco Mosaic Virus, which process comprises applying compounds of the following general formula I

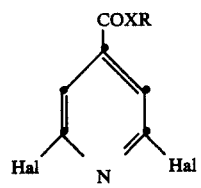

in which
Hal is halogen,
X is oxygen or sulfur, and
R is hydrogen, $C_1$–$C_6$-alkyl, $C_1$–$C_6$-alkyl which is interrupted by an oxygen, or sulfur, $C_1$–$C_6$-alkyl which is substituted by halogen, cyano or the COO-$C_1$–$C_6$-alkyl radical, $C_3$–$C_5$-alkenyl which is unsubstituted or substituted by halogen, $C_3$–$C_5$-alkynyl which is unsubstituted or substituted by halogen, $C_3$–$C_6$-cycloalkyl which is unsubstituted or substituted by halogen or methyl, or a normal equivalent of a cation which is formed from a base or a basic compound, as active ingredients in the rates of 100 g to 600 g per hectare to cereals, beets, pomes, drupes and soft fruits, legumes, oil crops, curcurbits, fibrous plants, citrus fruits, vegetable types, Lauraceae, tobacco, nuts, coffee plants or tea plants and/or their environment.

2. A method for immunizing healthy plants against the infestation of the plants by the fungi Oomycetes, *Fungi imperfecti* and Ascomycetes and the bacteria Pseudomonades, Xanthomonades and Erwinia and the Tobacco Mosaic Virus, which process comprises the dressing and/or coating of seeds by applying compounds of the formula I

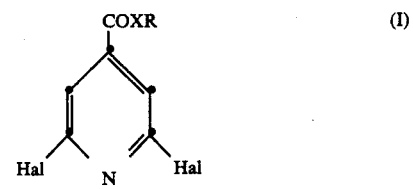

in which
Hal is halogen,
X is oxygen or sulfur, and
R is hydrogen, $C_1$–$C_6$-alkyl, $C_1$–$C_6$-alkyl which is interrupted by oxygen or sulfur, $C_1$–$C_6$-alkyl which ia substituted by halogen, cyano or the COO-$C_1$–$C_6$-alkyl radical, $C_3$–$C_5$-alkenyl which is unsubstituted or substituted by halogen, $C_3$–$C_5$-alkynyl which is unsubstituted or substituted by halogen, $C_3$–$C_6$-cycloalkyl which is unsubstituted or substituted by halogen or methyl, or a normal equivalent of a cation which is formed from a base or a basic compound, as active ingredients in rates of 50 g to 250 g per 100 kg seeds.

3. A method according to claim 1, in which Hal is chlorine or bromine, X is oxygen, and R is hydrogen, methyl, ethyl, n-propyl, iso-propyl or n-butyl or, as a normal equivalent of a cation: 4-[3-(4-tert.butylphenyl)-2-methylprop-1-yl]-2,6-dimethylmorpholine, N-[3-(4-tert.butylphenyl)-2-methylprop-1-yl]-piperidine or 4-cyclodecyl-2,4-dimethylmorpholine.

4. A method according to claim 2, in which Hal is chlorine or bromine, X is oxygen, and R is hydrogen, methyl, ethyl, n-propyl, iso-propyl or n-butyl or, as a normal equivalent of a cation: 4-[3-(4-tert.butylphenyl)-2-methylprop-1-yl]-2,6-dimethylmorpholine, N-[3-(4-tert.butylphenyl)-2-methylprop-1-yl]-piperidine or 4-cyclodecyl-2,4-dimethylmorpholine.

5. A method according to claim 3, in which Hal is 2,6-dichloro or 2,6-dibromo, and R is hydrogen, methyl or ethyl or, at a normal equivalent of a cation: 4-[3-(4-tert.butylphenyl)-2-methylprop-1-yl]-2,6-dimethylmorpholine or N-[3-(4-tert.butylphenyl)-2-methylprop-1-yl]-piperidine.

6. A method according to claim 4, in which Hal is 2,6-dichloro or 2,6-dibromo, and R is hydrogen, methyl or ethyl or, as a normal equivalent of a cation: 4-[3-(4-tert.butylphenyl)-2-methylprop-1-yl]-2,6-dimethylmorpholine or N-[3-(4-tert.butylphenyl)-2-methylprop-1-yl]-piperidine.

7. A method according to claim 5, which comprises using a compound selected from the group consisting of 2,6-dichloroisonicotinic acid; methyl 2,6-dichloroisonicotinate; ethyl 2,6-dichloroisonicotinate; and 2,6-dibromoisonicotinic acid.

8. A method according to claim 6, which comprises using a compound selected from the group consisting of 2,6-dichloroisonicotinic acid; methyl 2,6-dichloroisonicotinate; ethyl 2,6-dichloroisonicotinate; and 2,6-dibromoisonicotinic acid.

9. A compound of the formula $I^{IV}$

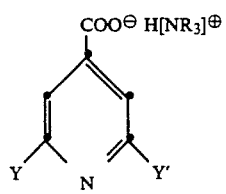

in which

Y and Y' are halogen, [NR₃] is an alkylamine having 1 to 3 (C₁–C₆)-alkyl groups or an alkylamine having 1 to 3 (C₁–C₆)-alkyl groups which is interrupted by an oxygen atom, or furthermore is one of the following cyclic alkylamines:

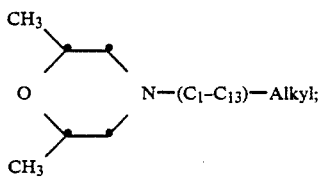

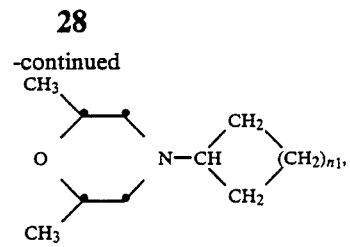

in which n₁ is 1–8;

in which n₁ is 1–8; including the enantiomers of the chiral structures of the cyclic alkylamines.

10. A compound from the group comprising: the salt of 2,6-dichloroisonicotinic acid with N-[3-(4-tert.butylphenyl)-2-methyl-n-prop-1-yl]-2,6-dimethylmorpholine; the salt of 2,6-dichloroisonicotinic acid with N-[3-(4-tert.butylphenyl)-2-methyl-n-prop-1-yl]-piperidine; propargyl 2,6-dichloroisonicotinate; cyclohexyl 2,6-dichloroisonicotinate; and methyl 2,6-difluoroisonicotinate.

11. A composition for protection against and prevention of infestation of plants by phytopathogenic microorganisms, comprising as active ingredient at least on compound of the formula $I^{IV}$ according to claim 9.

12. A composition according to claim 11, comprising as active ingredient at least one compound according to claim 10.

13. A composition according to claim 11, comprising 0.1 to 99% of an active ingredient of the formula I, 99.9 to 1% of a solid or liquid additive, and 0 to 25% of a surfactant.

14. A composition according to claim 13, comprising 0.1 to 95% of an active ingredient of the formula I, 99.8 to 5% of a solid or liquid additive, and 0.1 to 25% of a surfactant.

15. A method according to claim 1, which comprises using a compound selected from the group consisting of the salt of 2,6-dichloroisonicotinic acid with N-[3-(4-tert.butylphenyl)-2-methyl-n-prop-1-yl]-2,6-dimethylmorpholine, the salt of 2,6-dichloroisonicotinic acid with N-[3-(4-tert.-butylphenyl)-2-methyl-n-prop-1-yl]-piperidine; propargyl 2,6-dichloroisonicotinate; cyclohexyl 2,6-dichloroisonicotinate; and methyl 2,6-dicholoroisonicotinate.

16. A method according to claim 2, which comprises using a compound selected from the group consisting of the salt of 2,6-dichloroisonicotinic acid with N-[3-(4-tert.-butylphenyl)-2-methyl-n-prop-1-yl]-2,6-dimethylmorpholine the salt of 2,6-dichloroisonicotinic acid with N-[3-(4-tert.-butylphenyl)-2-methyl-n-prop-1-yl]-piperidine; propargyl 2,6-dichloroisonicotinate; cyclohexyl 2,6-dichloroisonicotinate; and methyl 2,6-difluoroisonicotinate.

* * * * *